United States Patent [19]
Borgert et al.

[11] Patent Number: 5,519,496
[45] Date of Patent: May 21, 1996

[54] ILLUMINATION SYSTEM AND METHOD FOR GENERATING AN IMAGE OF AN OBJECT

[75] Inventors: Gerald D. Borgert, Northville; Robert J. Bartlett, Ann Arbor; James F. Ellison, Brighton, all of Mich.

[73] Assignee: Applied Intelligent Systems, Inc., Ann Arbor, Mich.

[21] Appl. No.: 179,647

[22] Filed: Jan. 7, 1994

[51] Int. Cl.$^6$ ............................. G01B 11/00; G01N 21/88
[52] U.S. Cl. ............................. 356/394; 356/237; 348/126
[58] Field of Search ..................... 356/394, 372, 356/375, 376, 237, 240; 250/561, 562, 563, 571, 572, 223 B; 362/237, 249, 252, 11, 33, 800; 348/87, 94, 95, 126, 131; 382/8, 54, 55

[56] References Cited

U.S. PATENT DOCUMENTS

| | | | |
|---|---|---|---|
| 4,473,750 | 9/1984 | Oshida et al. | 356/376 |
| 4,677,473 | 6/1987 | Okamoto et al. | 356/376 |
| 4,688,939 | 8/1987 | Ray. | |
| 4,876,455 | 10/1989 | Sanderson et al.. | |
| 4,877,326 | 10/1989 | Chadwick et al.. | |
| 4,893,025 | 1/1990 | Lee. | |
| 4,893,223 | 1/1990 | Arnold. | |
| 4,929,845 | 5/1990 | Amir et al.. | |
| 4,972,093 | 11/1990 | Cochran et al. | 356/394 |
| 4,988,202 | 1/1991 | Nayar et al.. | |
| 5,030,839 | 7/1991 | van de Stadt. | |
| 5,038,258 | 8/1991 | Koch et al.. | |
| 5,058,178 | 10/1991 | Ray. | |
| 5,072,127 | 12/1991 | Cochran et al. | 356/394 |
| 5,083,863 | 1/1992 | Cerda. | |
| 5,113,565 | 5/1992 | Cipolla et al.. | |
| 5,115,475 | 5/1992 | Lebeau. | |
| 5,118,193 | 6/1992 | Brown et al.. | |
| 5,127,727 | 7/1992 | Arnold et al.. | |
| 5,170,062 | 12/1992 | Miyahara. | |
| 5,396,334 | 3/1995 | Sugawara | 356/394 |

FOREIGN PATENT DOCUMENTS

| | | | |
|---|---|---|---|
| 0218407 | 9/1991 | Japan | 356/376 |
| 4-166709 | 6/1992 | Japan | 356/371 |

*Primary Examiner*—Hoa Q. Pham
*Attorney, Agent, or Firm*—Dykema Gossett

[57] ABSTRACT

An illumination system having a lighting dome, a vertical light source, an image acquisition means, and a light controlling means, a system controller and a three-axis servo system wherein the dome is of unitary printed circuit board construction populated with a plurality of surface mounted light emitting diodes is disclosed. The dome has a first longitudinal axis and is bendable along hinges formed through the circuit board to define a partially enclosed dome having eight octants or sections, each section having an upper and lower tier portion defining a plurality of planar illumination banks, which illuminate an object from 360° around the object and from predetermined angles relative to the first longitudinal axis. The vertical light source, which is a planar printed circuit board populated with surface mounted LEDs, and the beam splitter are provided for illumination of the object with light parallel to the first longitudinal axis. The planar geometry of the illumination banks and the vertical lighting source cause the LEDs to emit light rays that are substantially parallel. The light controlling means controls the intensity of each section and tier portion through pulse width modulation of the respective plurality of light emitting diodes. The acquisition means is provided for acquiring reflected light rays to generate an image of the illuminated object. The increased density of the surface mounted diodes increase the light intensity produced over known illumination systems employing conventional LED mounting techniques. Moreover, the light controlling means can be programmed via the system controller to light any of the panels at a selected intensity. The system controller control the servo system to move the acquisition means in any of three axis so that the acquisition means can capture an image of a preselected area of the object. The system controller processes the captured image to detect a feature of the object.

9 Claims, 5 Drawing Sheets

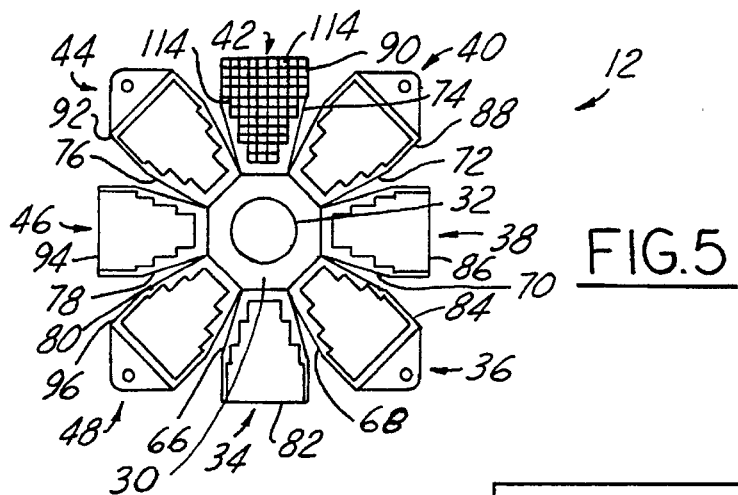
FIG.5
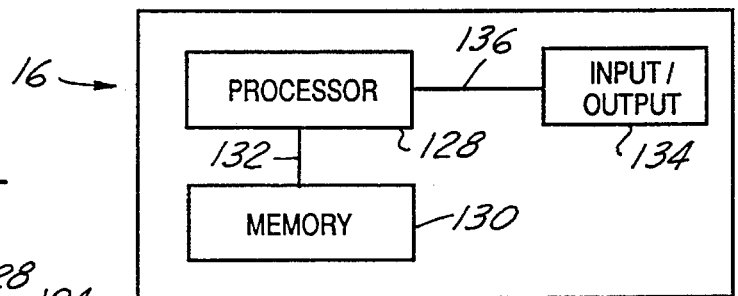
FIG.6
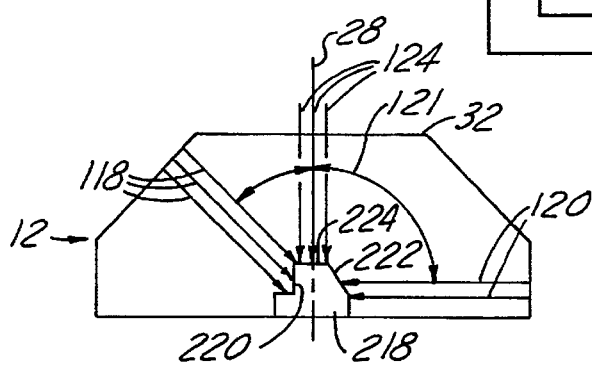
FIG.7
FIG.11

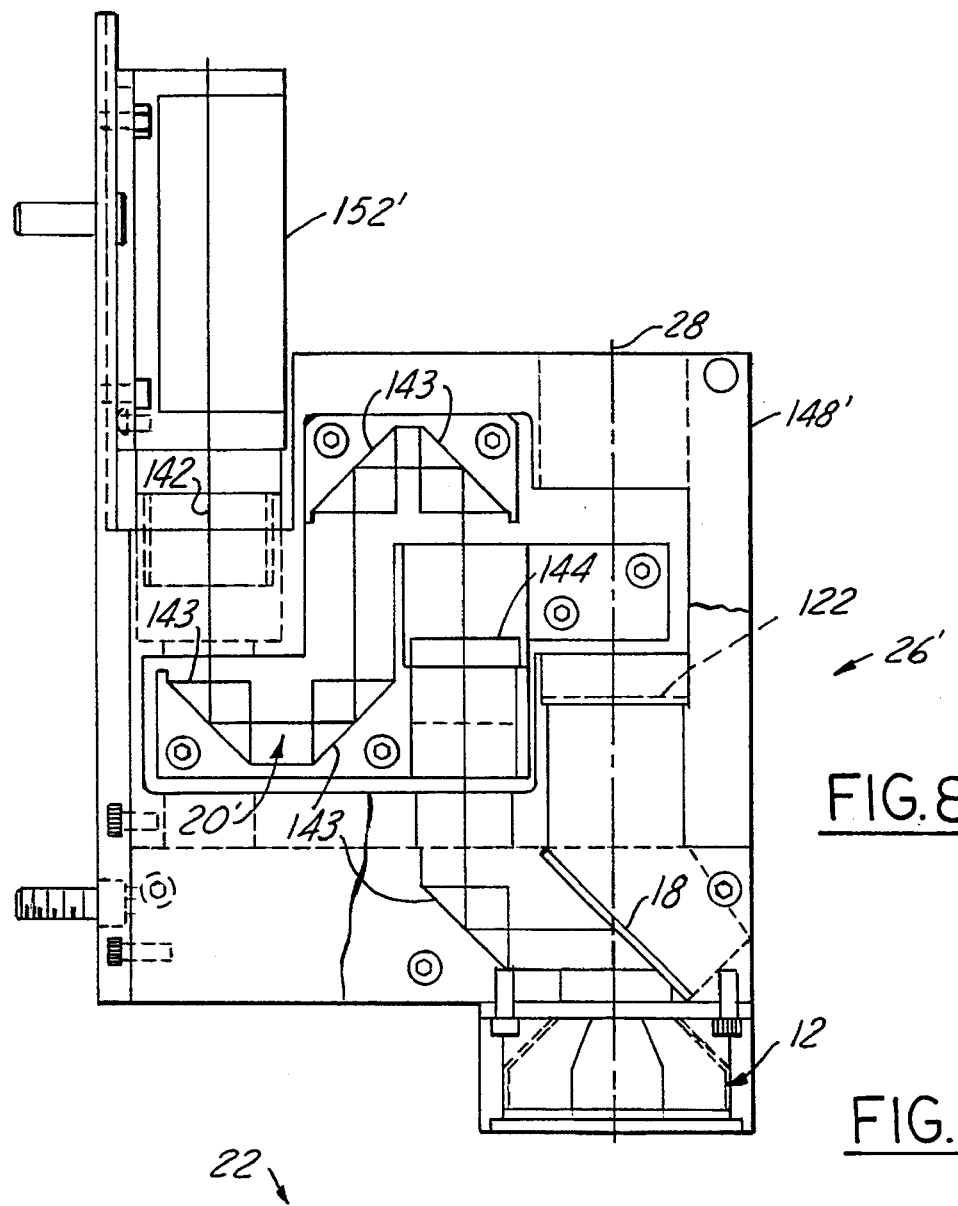
FIG.8
FIG.9
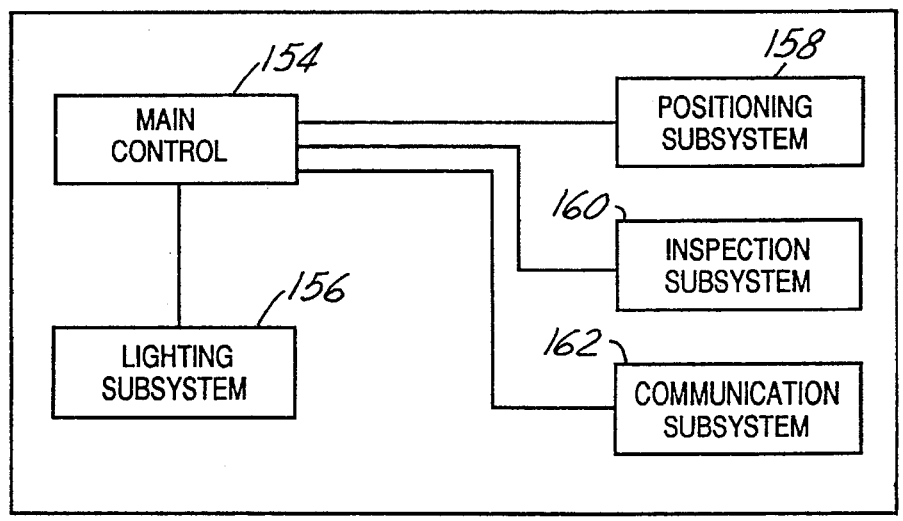

ILLUMINATION SYSTEM AND METHOD FOR GENERATING AN IMAGE OF AN OBJECT

TECHNICAL FIELD

This invention relates generally to an illumination system and method for generating an image of an object for use by inspection systems and the like.

BACKGROUND OF THE INVENTION

Prior art illumination systems range widely in their basic design depending on such factors as the desired use of the generated image, the general size and reflectivity of the object to be illuminated, and the specific features of the object sought to be captured. Such features include measurement of relative position, detection of specific shapes for analysis, and the detection of flaws or other imperfections. In order to capture and analyze such features, images of the object, or surfaces thereof, as well as images of the shadows cast by the objects are advantageously used by state of the art inspection systems. In prior art illumination systems employing annular light sources, which tend to provide a cone of light, the light is scattered and tends to illuminate surfaces which are not of interest for the inspection process. Other prior art illumination systems employing light sources whose rays converge upon the object being imaged also diminish the information obtainable by an attached inspection system because such converging light rays tend to distort or eliminate useful shadow images.

Moreover, known illumination systems typically employ machined blocks or other significantly complex and expensive to produce means for mounting conventional light sources (e.g., conventional mounted light emitting diodes). The cost involved in machining the mounting means, inserting the conventional light sources, the accompanying wiring and circuit lay-out and overall assembly time adds to the complexity and cost of such known illumination systems. A problem related to the above-mentioned conventional manufacturing problems is the insufficient light intensity produced by known illumination systems. Specifically, conventional light emitting diodes have a predetermined minimum mounting separation distance as employed in the prior art systems thus limiting diode placement density. It has been found that the relatively low diode density generates insufficient light intensity to provide adequate illumination for certain imaging and inspection applications.

Another problem in the prior art is the lack of flexibility in changing lighting patterns for different imaging applications.

Thus, there is a need for an improved illumination system for generating an image of an object that overcomes or minimizes the above-mentioned problems.

SUMMARY OF THE INVENTION

Use of an illumination source having means for emitting parallel light rays minimizes distortion of shadows cast by an object being illuminated by an illumination system having such a light source. Accordingly, in one aspect of this invention, an illumination system comprising a lighting dome, a vertical light source, a beam splitter, a controlling means, and an acquisition means is disclosed. The lighting dome is provided with a plurality of planar illumination banks, each one of the banks having a plurality of light emitting diodes mounted thereon, the plurality of diodes being disposed on the respective illumination banks to emit substantially parallel light rays at predetermined angles to an axis coincident with the acquisition means line of sight to illuminate the surface of the object. Further, in order to illuminate the surface of the object with light rays parallel to the above-mentioned axis, the vertical light source is provided with another plurality of light emitting diodes mounted thereon to emit substantially parallel light rays, and the beam splitter is positioned intermediate the vertical light source and the lighting dome for directing light rays from the vertical light source to the surface of the object in a path substantially parallel to the above-mentioned axis.

It has been found that surface mount device manufacturing techniques can significantly increase the density of the devices mounted thereby. Accordingly, in another aspect of this invention, the plurality of light emitting diodes mounted to each one of the plurality of planar illumination banks are of the surface mount device type, and are surface mounted to the illumination bank. Use of this surface mount device technology provides a large increase in the light emitting diode density, thus providing a commensurate increase in the maximum light intensity provided by the lighting dome.

In another aspect of the present invention, the lighting dome is of unitary printed circuit board construction. The ability to fabricate the lighting dome by surface mounting the LEDs to the printed circuit board, and bending the circuit board into its predesigned shape reduces the costs and complexity relative to known illumination systems.

In another aspect of this invention, a system controller is provided to coordinate movement of the object relative to the acquisition means with preselected lighting configurations.

Other objects, features and advantages will become clear or will be made apparent during the course of the following description of a preferred embodiment of the present invention.

BRIEF DESCRIPTION OF THE DRAWINGS

FIG. 5 is a bottom plan view of the illuminating apparatus shown in FIG. 1, showing an exemplary illumination bank;

FIG. 6 is a functional block diagram of the light controlling means portion of the illumination system shown in FIG. 1;

FIG. 7 is a view of the lighting dome depicted in FIG. 1 showing a preferred range of illumination angles;

FIG. 8 is a view of a preferred embodiment of the present invention incorporating a preferred image acquisition means and a preferred mounting assembly;

FIG. 9 is a functional block diagram of the system controller of FIG. 1 depicting several functional subsystems;

FIG. 11 is a view of a input lighting configuration window which appears on the screen of the monitor shown in FIG. 1.

DETAILED DESCRIPTION

Figure 1:
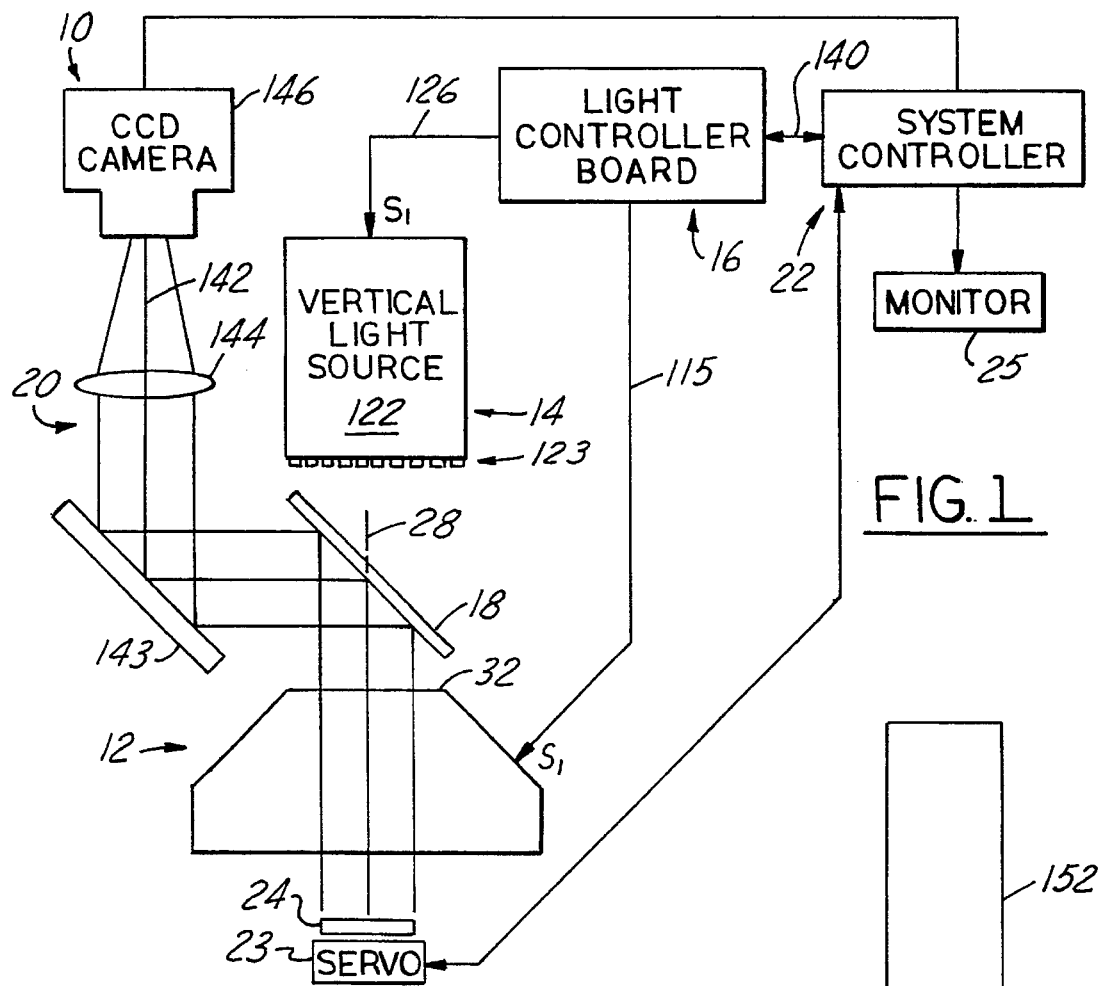
FIG. 1 is a functional block diagram of an illumination system of the present invention incorporating an illumination apparatus.

Referring now to the drawings wherein like reference numerals reference identical components in the various views, FIG. 1 is a functional block diagram of an illumination system 10 according to the present invention. The illumination system 10 is comprised of an oblique illumination means, preferably taking the form of an oblique lighting dome 12, a vertical light source 14, a light controlling means 16, a beam splitter 18, an image acquisition means 20 for capturing the reflected image of an object under illumination, a means or device for communicating with light controlling means 16, preferably a system controller 22, a means for effecting relative movement between an object and acquisition means 20, preferably an x-y-z axis servo controller 23, a first object 24 and a monitor 25.

Figure 2:
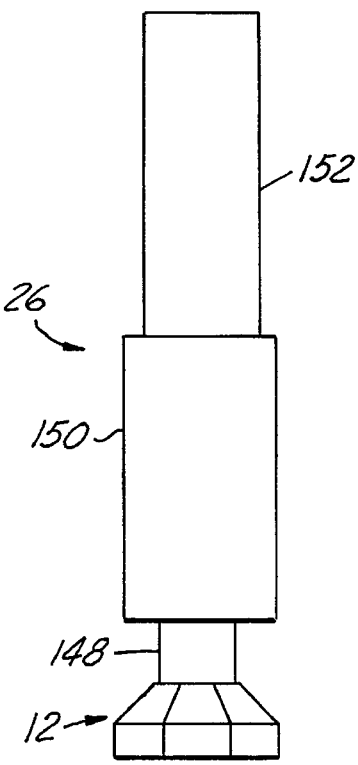
FIG. 2 is a view, not to scale, of a subassembly of the inventive illumination system showing a camera housing fixedly mounted to the illumination apparatus shown in FIG. 1.

As shown in FIG. 2, mounting assembly 26 comprises lighting dome 12 and serves to fixedly mount image acquisition means 20 to lighting dome 12 so that acquisition means 20 stays aligned with lighting dome 12 when mounting assembly 26 is moved relative to first object 24 while under inspection.

Figure 4:
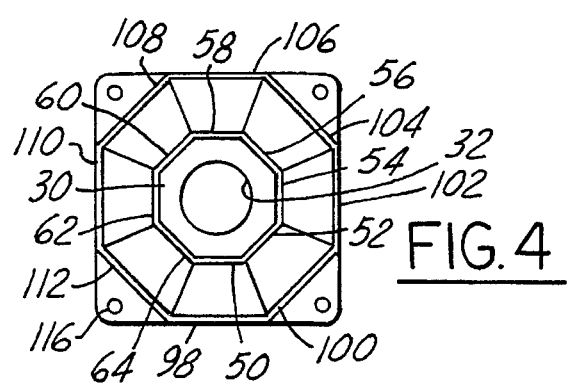
FIG. 4 is a top plan view of the illuminating apparatus shown in FIG. 1.
Figure 3:
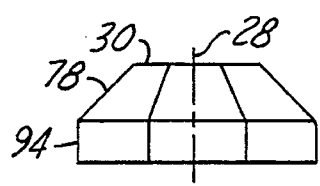
FIG. 3 is a front elevational view of the illuminating apparatus shown in FIG. 1.

The lighting dome 12 is provided in illumination system 10 for illuminating first object 24 such that acquisition means 20 may capture a reflected image. It should be understood that the term dome is exemplary only, and that other shapes for emitting substantially parallel light rays comes within the spirit and scope of this invention. Referring now to FIGS. 3, 4 and 5, dome 12 is generally elongated and includes a first longitudinal axis 28. The dome 12 is of unitary printed circuit board (PCB) construction, shown in an unfolded state in FIG. 5, and in a folded, assembled state in FIGS. 3 and 4. The dome 12 includes a thin planar top portion 30, preferably taking the form of an octagon and including an opening 32 formed therethrough to allow light rays reflected from first object 24 to reach beam splitter 18. In an assembled state, top portion 30 is generally perpendicular to first longitudinal axis 28, and the central axis of opening 32 is generally coincident with first longitudinal axis 28. As best shown in FIG. 5, the unitary dome 12 has preferably eight elongated sections or octants 34, 36, 38, 40, 42, 44, 46 and 48, that are circumferentially spaced about top portion 30 and connected thereto by a plurality of first hinges 50, 52, 54, 56, 58, 60, 62 and 64, best shown in FIG. 4. As shown in FIG. 3, each section or octant is generally longitudinally extending relative to first longitudinal axis 28. The plurality of first hinges 50, 52, 54, 56, 58, 60, 62 and 64, are so-called living hinges defined by bend lines formed through the PCB of dome 12.

As shown in FIG. 5, each of the sections 34, 36, 38, 40, 42, 44, 46 and 48 includes a respective top or upper tier portion 66, 68, 70, 72, 74, 76, 78 and 80 and bottom or lower tier portion 82, 84, 86, 88, 90, 92, 94 and 96, separated by a respective one of a plurality of second hinges 98, 100, 102, 104, 106, 108, 110 and 112 (FIG. 4), the upper tier portions collectively defining an upper tier of dome 12, while the lower tier portions collectively defining a lower tier of dome 12. As shown in FIG. 3, the completed dome 12 is formed from the printed circuit board by folding each upper tier portion about its respective first hinge and folding each lower tier portion about its respective second hinge until a partially enclosed dome is formed.

Referring now to FIG. 5, each upper and lower tier portion of dome 12 includes a first plurality of surface mounted light emitting diodes (LEDs) 114 illustrated only in section 42 for purposes of convenience. LEDs are very efficient and require very low power as compared to tungsten and other illuminating sources. Each first plurality of LEDs 114 is wired separately to define an illumination bank. The LEDs used to populate the illumination banks are of the surface mount device (SMD) type and are preferably surface mounted to dome 12 to emit a narrow band wavelength of light, preferably having a nominal center wavelength of 660 nanometers. Each first plurality of LEDs 114 is wired for individual activation by application of signal $S_1$ by light controlling means 16 through connection means 115. The dome 12 includes a plurality of mounting bores 116.

Referring now to FIGS. 1, 3 and 4, the several planar illumination banks of dome 12 are arranged at various angles 360° around first object 24, and at various angles with respect to first longitudinal axis 28. As shown in FIG. 7, illumination banks mounted on an upper tier portion emit light rays oblique to the object being imaged, shown as oblique rays 118, forming an acute angle 119 with first longitudinal axis 28. Similarly, illumination banks mounted on a lower tier portion selectively emit light rays that are perpendicular to first longitudinal axis 28, shown as perpendicular rays 120, forming right angle 121 with first axis 28. The full import of this oblique illumination will be discussed below.

The vertical light source 14 is provided in illumination system 10 for illuminating first object 24 with light rays parallel to first longitudinal axis 28, which is particularly useful for enhancing the return of light from surfaces of first object 24 that are normal to first longitudinal axis 28. As shown in FIG. 1, light source 14 includes printed circuit board 122 populated with a second plurality of surface mounted LEDs (not shown) similar to the first plurality of LEDs 114. Light source 14 emits light rays that are substantially parallel to first longitudinal axis 28, shown as parallel rays 124 (FIG. 7). As shown in FIG. 1, light emitted from light source 14 passes through beam splitter 18. In addition to this light transmission feature, beam splitter 18 performs a second function in system 10 to be described below. The second plurality of LEDs surface mounted to printed circuit board 122 is responsive to actuation signal $S_1$ applied by light controlling means 16 through connection means 126.

Referring now to FIG. 6, light controlling means 16 includes processor means 128, memory means 130 coupled with processor means 128 by coupling means 132, and input/output or interface means 134 coupled with processor means 128 by coupling means 136. The processor means 128 preferably includes a Motorola M68HC11 processor, and is responsible for selectively causing any one of the illumination banks of dome 12, and/or light source 14, to emit light by applying a respective actuation signal $S_1$ thereto. The memory means 130 preferably takes the form of an electrically-erasable programmable read-only memory (EEPROM), and is used to store a variety of predetermined operating and configuration information. Interface means 134 is provided for enabling external control by a user of dome 12 through system controller 22, and preferably includes conventional serial communications port, such as an RS-232 serial port. Moreover, interface means 134 preferably includes a digital port to enable hardware reset and for strobing preselected illumination banks of dome 12 when system 10 is in a strobe mode, a mode to be discussed in further detail below. When in a continuous mode, also to be discussed below, the assertion of the strobe line of the digital port is not effective to strobe the above-mentioned banks. As shown in FIG. 1, light controlling means 16 is connected with system controller 22 by connection means 140.

Referring now to FIG. 1, image acquisition means 20 is in optical communication with the surface of first object 24, its line of sight being effectively coincident with first axis 28, and is provided in system 10 for capturing light rays reflected from first object 24 in response to first object 24 being illuminated in order to produce an image of the object for use by an inspection system or the like. It should be understood by one of ordinary skill in the art that there exists a plurality of optical configurations to effect the above-mentioned functions of acquisition means 20. In one embodiment, however, acquisition means 20 includes a second longitudinal axis 142 that is substantially parallel to first longitudinal axis 28, but is offset therefrom, a first surface mirror 143, a lens 144, and a camera 146. Also included in acquisition means 20 is beam splitter 18. In addition to its light transmission function, beam splitter 18 transfers the image of first object 24 to mirror 143. The mirror 143 is used to transfer the image of the object reflected from beam splitter 18 to lens 144. The lens 144 magnifies and focuses the image transferred by mirror 143 by respective predetermined amounts. The camera 146 is used to capture the focused image directed from lens 144. The beam splitter 18, mirror 143, lens 144, and camera 146 are all conventional in the art. Preferably, camera 146 is a charge-coupled device (CCD) camera wherein each of the CCDs within camera 146 serves to capture the image of a small picture element so that an array of CCDs collectively captures the image of an area of first object 24 lying within its field of view. Further, camera 146 preferably has a bandwidth, approximately 600 to 700 nanometers, within which its sensitivity is greatest. Thus, system 10 optimizes illumination and image acquisition by selecting LEDs whose nominal wavelength (660 nm) falls within the above-mentioned bandwidth, thus increasing acquisition means gain.

Referring now to FIG. 2, mounting assembly 26 includes optics housing 148, extension housing 150, and camera housing 152. As previously mentioned, the purpose of mounting assembly 26 is to maintain a fixed relationship between lighting dome 12 and acquisition means 20, including camera 146, which is mounted within camera housing 152. The advantages of maintaining the alignment between camera 146 and lighting dome 12 are obvious when system 10 is used in an environment where the object under inspection is stationary and the inspection system must move.

A preferred embodiment of the image acquisition means 20 and the mounting assembly 26 is shown in FIG. 8 as image acquisition means 20' and mounting assembly 26'. The advantage of the preferred embodiment is that the mechanical distance between the camera and the lighting dome 12 is reduced, although the optical or focal distance is not. This folding of light is accomplished through the use of five mirrors 143, and lens 144. As shown in FIG. 8, reflected light emerging from dome 12 is reflected from beam splitter 18 to one of the mirrors 143. The reflected light rays then travel through lens 144 and then through four mirrors 143 and then to camera 146, as shown by the solid line indicating the image path. The mounting assembly 26' includes an optics housing 148' and a camera housing 152'. In this preferred embodiment, extension housing 150, shown in FIG. 2, has been eliminated due to the folding of the light rays reflected from the object under illumination.

Referring now to FIG. 9, the purpose of system controller 22 is to coordinate the various subsystems of illumination system 10 for a particular application. System controller 22 includes a main control subsystem 154, a lighting subsystem 156 coupled with main control 154, a positioning subsystem 158 coupled with main control 154, an inspection subsystem 160 coupled with main control 154 and a communication subsystem 162 also coupled with main control 154. The system controller 22 can take many forms, but is preferably shown as a commercially available unit, particularly Model 3500 EX available from Applied Intelligent Systems Incorporated, based in Ann Arbor, Mich. The function of lighting subsystem 156 is to control light controlling means 16 for purposes of selectively activating one of the lighting configurations, to be discussed below, stored in memory means 130 for illuminating an object. The function of positioning subsystem 158 is to control servo 23 to effect relative movement between object 24 and image acquisition means 20. The inspection subsystem 160 is provided in system controller 22 to process a signal generated by CCD camera 146 wherein the signal is representative of the image captured by camera 146, to detect a feature, such as a ball bond joint, or a wiring lead location, and to decide whether the object or part under inspection is bad based upon predetermined criteria. The inspection subsystem 160 may include intelligent algorithms that process several images, each of the images perhaps having a unique lighting configuration and camera position associated therewith, in making its decision. These algorithms may be of the type that weights each of the images according to predetermined values, or may make its decision on statistical grounds (e.g., the part passes inspection when a majority, for example, three out of five, of the images pass the predetermined criteria). The communication subsystem 162 is provided in system controller 22 to allow effective communication between the system controller 22 and light controlling means 16, servo 23, and camera 146.

The means for effecting relative movement or servo controller 23 is provided in system 10 to move either first object 24 relative to system 10 or move system 10 relative to part 24. As shown in FIG. 1, servo 23 is therein adapted to move object 24. Preferably, however, servo system 23 is adapted to move the optical components, the illumination components, and the image acquisition means of system 10 relative to first object 24. Preferably, servo system 23 includes a three-axis servo controller controlling three servo motors, one for the x axis, one for the y axis, and one for the z axis. Positioning subsystem 158 of system controller 22 allows detailed control of servo system 23. The nature and magnitude of the movement is controlled by six parameters used by positioning subsystem 158. A user may specify movement in terms of a three parameter x-y-z coordinate. In addition a user must indicate whether the specified coordinates are relative to the current position, or are absolute coordinates. Further, a user may define the acceleration and the speed with which the movement takes place. Once a user has specified these parameters, positioning subsystem 158 processes this information and sends the three-axis servo controller a command through a serial port through communication subsystem 162. The three-axis servo controller accepts the command and activates the x, y, and z, servos accordingly. When the servo controller has completed its operation, it sends a signal back to system controller 22 to acknowledge completion of the command.

The path of the reflected image of an object will now be described. Referring now to FIG. 1 and FIG. 7, illumination of first object 24 is accomplished by using dome 12 and light source 14. The dome 12 illuminates first object 24 from all sides (i.e., 360° around first object 24 to be viewed by acquisition means 20). The light source 14 illuminates first object 24 along first axis 28, which is also the effective axis of the line of sight of camera 146. The light emitted from each one of the sections 34, 36, 38, 40, 42, 44, 46 and 48 and its respective upper and lower tier illumination banks are individually controlled by light controlling means 16 by way of actuation signal $S_1$. When light controlling means 16 applies signal $S_1$ to a particular illumination bank comprising one of the first plurality of LEDs of lighting dome 12, oblique illumination of first object 24 occurs wherein light emitted from the preselected illumination banks reach the surface of first object 24. The reflected light rays travel upwardly along first longitudinal axis 28 to reach beam splitter 18. The reflected light rays representing an image of first object 24 are then reflected from beam splitter 18 to first surface mirror 143, then to lens 144 and finally captured by camera 146 to generate an image of first object 24. On-axis illumination is achieved by directing light from vertical light source 14 through beam splitter 18, through opening 32 and finally to first object 24. The light emitted from vertical light source 14 occurs in response to light controlling means 16 applying signal $S_1$. Light rays representing the image of first object 24 then reflect up to beam splitter 18, then to first surface mirror 143, and finally to lens 144 and camera 146.

The light controlling means 16 comprises two modes of operation: continuous mode and strobe mode. In continuous mode, the light intensity emitted from any plurality of light emitting diodes under control of controlling means 16 located in either vertical light source 14 or lighting dome 12, can be varied from a predetermined minimum intensity to a predetermined maximum intensity through the pulse width modulation (PWM) of signal $S_1$ to the desired LEDs. For example, to effect a predetermined intensity from upper tier portion 66 of lighting dome 12, light controlling means 16 applies a continuous pulse width modulated signal $S_1$ to upper tier portion 66 for a predetermined interval. Since each upper tier, lower tier, section, and vertical light source 14 are individually controlled, the respective plurality of LEDs may also be varied with respect to the light intensity level.

The second mode of operation, strobe mode, is provided for minimizing or reducing the defocusing effect of motion of an object being illuminated. In other words, in the strobe mode, motion is frozen by the strobing of preselected illumination banks and/or of light source 14 for providing an image of greater clarity which may be captured by camera 146. In strobe mode, light controlling means 16 causes a preselected illumination bank or vertical light source 14 to output a single pulse of light at full intensity for a specified duration. Strobe mode is accomplished via actuation signal $S_1$ through connection means 115 and 126. Moreover, memory means 130 of light controlling means 16 has the capability of storing 128 individual preselected lighting programs or configurations implementing any combination of the continuous and strobe modes, wherein intensity and duration of each of the illumination banks mounted in lighting dome 12 and vertical light source 14 are defined.

Figure 10:
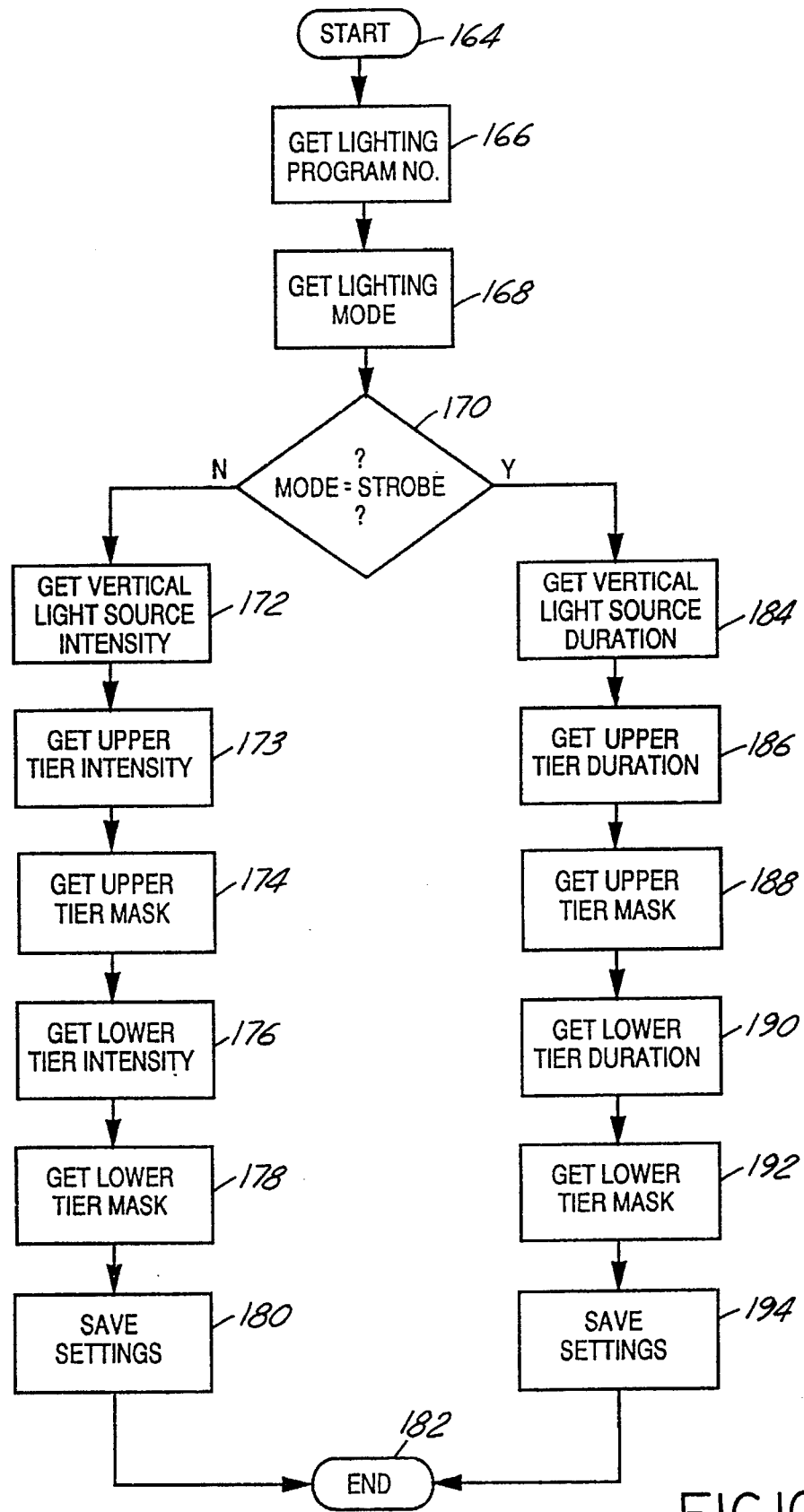
FIG. 10 is a flow diagram of a lighting routine used by the lighting subsystem of FIG. 9.

More particularly, each program is defined by six parameters: the mode, either continuous or strobe, the vertical light source intensity when in continuous mode or a duration for which the vertical light source is pulsed when in strobe mode, the top tier intensity when in continuous mode or the duration for which the top tier is pulsed when in strobe mode, the top tier mask or, in other words, those top or upper tier portions that are selected to emit light, the bottom or lower tier intensity when in continuous mode or the duration for which the bottom tier is pulsed in strobe mode, and the bottom or lower tier mask, or in other words those bottom or lower tier portions that are selected to emit light. Referring now to FIG. 10, the method by which lighting subsystem 156 of system controller 22 obtains the above-identified six parameter values is depicted. The method begins in a start or initial state 164. In step 166, the lighting subsystem 156 gets the program number, which defines which of the 128 lighting programs or configurations will be programmed with the information to be obtained. In step 168, the mode is obtained. In step 170, a test is performed wherein it is determined whether strobe mode or continuous mode was obtained in step 168. If continuous mode was obtained in step 168, then the method proceeds to step 172, where the vertical light source intensity is inputted. In step 173, the upper tier intensity is inputted.

It should be understood that the illumination banks of lighting dome 12 have a predetermined minimum and maximum light intensity levels. A preferred method allows input of a percentage wherein zero is the setting for no light and 100 is the setting for maximum light intensity. Alternatively, zero is the setting for no light and 255 is the limit for maximum light intensity. In step 174, lighting subsystem 156 obtains the upper or top tier mask which is used by the lighting subsystem 156 to determine which of the upper tier portions of dome 12 should be illuminated. In step 178 the value for the lower tier intensity and the lower tier mask are obtained by the lighting subsystem. In step 180, the above settings are saved in the memory means 130 of light controlling means 16 by the issuance of a command by system controller 22 through its communication subsystem 162, in particular one of the RS232 serial ports, to light controlling means 16. Processor means 128 is programmed to recognize a set of predefined commands that can be issued from system controller 22, one of which is the save settings command. The method ends in step 182. Alternatively, in step 170, if the mode was determined to be the strobe mode, then an alternate path is taken beginning with step 184, wherein the vertical light source duration is obtained by lighting subsystem 156. In steps 186 and 188, the upper tier duration and the upper tier mask are respectively obtained. In steps 190 and 192 the lower tier duration and the lower tier mask are respectively obtained. In step 194 the settings obtained in steps 184–192 are saved in a fashion similar to step 180 under a program number obtained in step 166.

It should be understood that in strobe mode the vertical light source, the upper tier, and the lower tier, can each be defined to have a particular duration, expressed as a percentage of a period. Preferably, in the strobe mode the cycle repeats every 16 milli-seconds. Thus, for example, if the vertical light source duration equals 10%, the upper tier duration equals 20%, and the lower tier duration equals 30%, then the following will result. Prior to initiation of strobe mode, the upper and lower tiers as well as the vertical light source will not be lit. The light controlling means 16 then sets the strobe mode by a command issued by system controller 22 through its serial port. Strobe mode is then actuated by assertion of one of the above-mentioned digital lines. Once strobe mode is initiated, the vertical light source, those upper tier portions selected to emit light, and those lower tier portions selected to emit light, will turn on. After 10% of the 16 milli-second strobe cycle has elapsed, the vertical light source duration parameter will have expired, and light controlling means 16 will send a signal via connecting means 126 to extinguish the vertical light source. After 20% of the 16 milli-second strobe cycle has elapsed, light controlling means 16 will turn off those upper tier portions that were previously turned on. After 30% of the 16 milli-second cycle has elapsed, light controlling means 16 will turn off those lower tier portions that had been previously turned on. For the remaining 70% of the 16 milli-second strobe cycle, all the light sources will be turned off. All of these light sources will emit light at full intensity. Once a new cycle has started, the above sequence of turning on and turning off of the various light sources will be repeated until either the strobe mode actuation signal via the digital line is removed, or strobe mode is changed to continuous mode via system controller 22 through the serial port.

As shown in FIG. 11, an input window utilized by the lighting subsystem 156 for the input of the above-mentioned program or configuration settings is depicted. The program settings obtained by the lighting subsystem 156 for use in programming light controlling means 16 may be obtained from two sources. The first source is from a higher level software application. For example, in a wire bond inspection application, a higher level application software can predefine the various lighting program configurations to meet its particular requirements. Alternatively, any lighting configuration may be defined and executed in real time through the use of the input lighting configuration window 196. A user can selectively cause window 196 to appear on monitor 25 through use of a mouse (not shown) or a keyboard (not shown), or any other appropriately conditioned input device attached from system controller 22. As shown in FIG. 11, window 196 has a field 198 wherein the program number may be entered by a user, through either entry from a keyboard or by clicking the button on a mouse. The window 196 also includes fields 200 and 202, for selection of either the continuous or a strobe mode, for example by positioning the cursor over one of the fields and clicking the mouse. The window 196 also includes a field 204 for setting the vertical light source intensity when in continuous mode, or for setting the vertical light source duration as a percentage when strobe mode is selected. The window 196 further includes fields 206 and 208 for respectively setting the top tier and bottom tier intensity level when in continuous mode or setting the duration percentage when in strobe mode. The window 196 also includes fields 210 and 212 for selecting the tier portions that a user desires to be illuminated. Clicking the center box within field 210 or 212 will select all eight boxes around the perimeter, thus selecting all of the upper or top tier portions or all of the lower or bottom tier portions respectively. The window 196 further includes a field 214, which, when selected, will save the above-defined program settings in the program number defined in field 198 in memory means 130 of light controlling means 16. Field 216, when selected by user, will send a predefined sequence of commands from system controller 22 to light controlling means 16, wherein light controlling means 16 will execute the commands, thus performing the diagnostic.

Light controlling means 16 has the capacity, through interface means 134, for accepting command signals from system controller 22 that are processed by processor means 128 to recall and implement any of the above-mentioned predetermined individual lighting configurations. Moreover, processor means 128 has the capability of accepting, in real time, commands from system controller 22 through connecting means 140 to activate any of the illumination banks of lighting dome 12, or of the second plurality of LEDs mounted on printed circuit board 122 of vertical light source 14. The interface means 134, as mentioned previously, preferably provides at least one digital port to system controller 22 through connecting means 140. This digital port is of a conventional interrupt line type that allows a user working from system controller 22 to initiate strobe mode by asserting the interrupt line.

Referring now to FIG. 7, an irregularly shaped second object 218 is shown under the illumination provided by lighting dome 12 where it can be seen that oblique rays 118 illuminate first surface 220, perpendicular rays 120 illuminate second surface 222, and parallel rays 124 illuminate third surface 224. As should be understood from the figure, use of planar illumination banks such as those emitting oblique rays 118, will cause a shadow to be cast by second object 218' such that acquisition means 20 captures the image of the shadow through its line of sight, thus enhancing an inspection system's ability to detect a feature, such as a flaw or imperfection.

Figure 12:
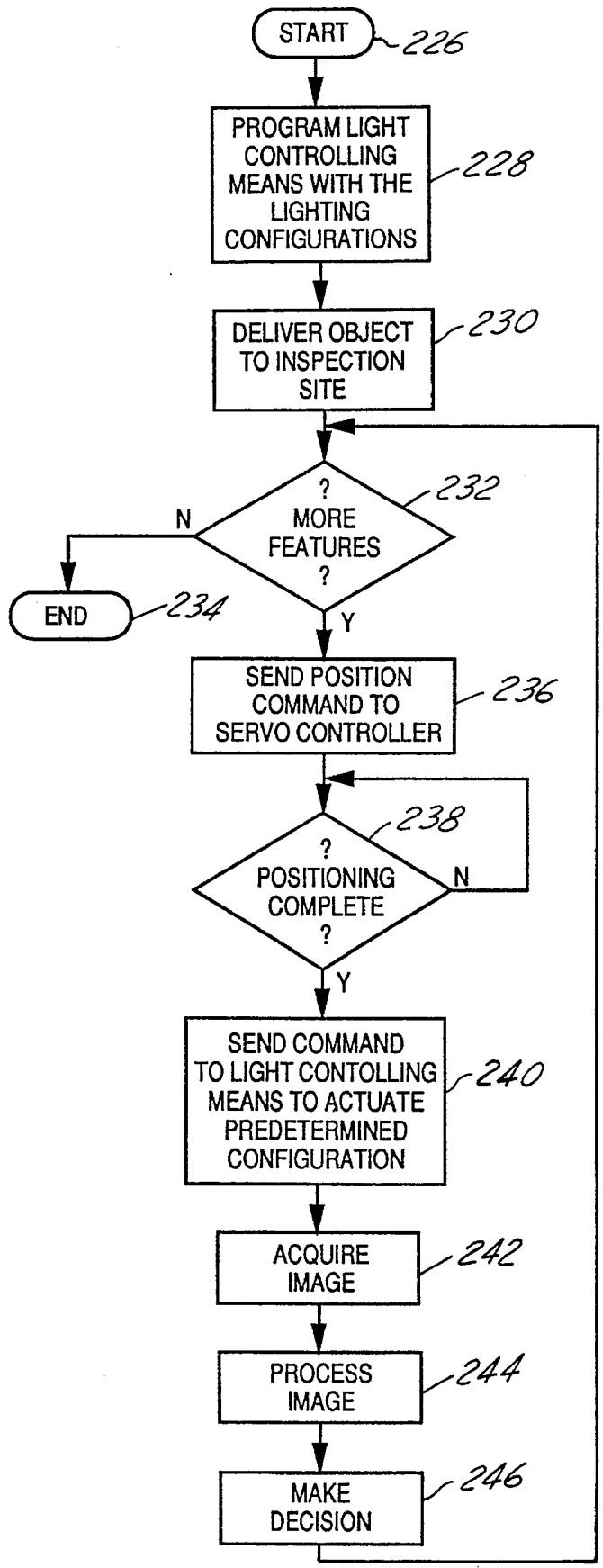
FIG. 12 is a flow diagram of a method of inspecting an object according to the present invention.

The overall method of inspecting a part in accordance with the present invention will now be described. Referring now to FIG. 12, the method begins in a start state 226. In step 228, the memory means 130 of light controlling means 16 is programmed to define particular lighting configurations in accordance with the flow diagram of FIG. 10. For many typical applications, such as a wire bond inspection, the settings for the particular desired lighting configurations are predefined by a high level software application program running under main control 154 of system controller 22. Once these configurations are downloaded through the serial port of system controller 22, the lighting configurations for the particular application are defined and ready to be recalled and executed by light controlling means 16 by a single-byte command issued by system controller 22. It is advantageous that these predefined lighting configurations be recalled and implemented with a very short command because in many applications, for throughput efficiencies, the program and the accompanying image acquisition and image processing must all occur within a very short period of time, and the use of a single byte command facilitates quick activation.

In step 230, positioning subsystem 158 delivers the object to be inspected to a known predetermined position within illumination system 10. For example, consecutive parts are a predefined distance apart from each other, and thus the positioning means moves the previously-inspected part down the line and delivers the object to be tested into the predefined inspection position. In step 232 a test is performed to determine whether all the features of the object have been inspected. For a particular application, there may be a plurality of features to be inspected on a particular part. For each of these features, there is a predetermined optimal image acquisition position and a corresponding lighting configuration. Therefore, a loop is performed until all the desired features for that particular object have been inspected. In step 236, the corresponding position for the feature to be inspected is sent by main control 154 via the positioning subsystem 158 and communication subsystem 162 to servo 23. Execution of the inspection process is temporarily halted while positioning subsystem 158 waits for an acknowledgement from servo 23 that the commanded position has been reached. Upon receiving acknowledgement from servo system 23, control continues to step 240 where lighting subsystem 156, through communication subsystem 162, sends a command to light controlling means 16 for actuating the above-mentioned corresponding lighting configuration. In step 242, while dome 12 emits light in accordance with the predetermined lighting configuration, the image acquisition means 20 captures light rays reflected from the object being inspected and generates a signal that is representative of that captured image. In step 244, inspection subsystem 160 processes the signal that is representative of the captured image, according to predetermined algorithms for the application at hand. In step 246, inspection subsystem 160 makes some decision based upon the result of the processing performed in step 244. For example, a message may be sent to monitor 25 indicating to the operator that the object or part under test has failed and should be tagged as bad, or system controller 22 may be programmed to automatically uplink with a host computer for delivering the decision and the accompanying details so that the host computer (not shown) may make a note of this failed test in a database for further action.

It is to be understood that the above description is merely exemplary rather than limiting in nature, the invention being limited only by the appended claims. Various modifications and changes may be made thereto by one of ordinary skill in the art which will embody the principals of the invention and fall within the spirit and scope thereof.

What is claimed is:

1. An apparatus for illuminating an object comprising:
   a lighting dome having a longitudinal axis, said dome including a plurality of illumination banks, each one of said banks having at least a first plurality of light emitting means mounted thereon, said first plurality of light emitting means being arranged on said illumination bank to emit substantially parallel light rays toward the object;
   a vertical light source having a second plurality of light emitting means mounted thereon, said second plurality of light emitting means being disposed on said vertical light source for emitting substantially parallel light rays coincident with and radially extending from said longitudinal axis;
   a beam splitter optically intermediate said dome and said vertical light source for directing light rays in a path coincident with and radially extending from said longitudinal axis through said dome to the surface of the object;
   light controlling means coupled with said illumination banks and said vertical light source for causing said first and second pluralities of light emitting means to emit light rays for illuminating the surface of the object; and,
   image acquisition means in optical communication with the surface of the object for capturing light rays reflected from the object in response to the object being illuminated to produce an image of the object.

2. The apparatus of claim 1, wherein said dome includes a top portion substantially perpendicular to said axis and a plurality of longitudinally extending sections circumferentially spaced about said top portion and connected thereto by one of a plurality of first hinges, each one of said plurality of sections having an upper and lower tier portion separated by one of a plurality of second hinges wherein each one of said upper and lower tier portions includes one of said plurality of illumination banks.

3. The apparatus of claim 2, wherein said dome is of unitary printed circuit board (PCB) construction and each first plurality of light emitting means includes a first plurality of light emitting diodes, and wherein each one of said plurality of illumination banks has surface mounted thereto one of said first plurality of light emitting diodes, said pluralities of first and second hinges comprising bend lines formed in the unitary PCB to thereby simplify construction of said dome.

4. The apparatus of claim 2, wherein said dome includes eight sections and wherein said lower tier portion is substantially parallel to said axis and said upper tier portion forms an acute angle with respect to said axis such that the object is obliquely illuminated by light rays.

5. The apparatus of claim 2 further comprising means for reducing a longitudinal distance between said dome and said image acquisition means while maintaining a focal length associated with said image acquisition means.

6. The apparatus of claim 1, wherein said light controlling means is of the type including a continuous mode wherein the intensity of light rays emitted from said illumination banks and said vertical light source is variable from a predetermined minimum to a predetermined maximum intensity level by said light controlling means.

7. The apparatus of claim 6, wherein said light controlling means causes light rays to be emitted from said illumination banks and said vertical light source by applying a respective actuation signal thereto, the intensity of the respective emitted light rays being variable by pulse width modulation of said respective actuation signal by said light controlling means.

8. The apparatus of claim 1, wherein said light controlling means is of the type including a strobe mode wherein the intensity of light rays emitted from said illumination banks and from said vertical light source is equal to said predetermined maximum intensity, said vertical light source emitting light rays for a first predetermined interval, selected ones of said illumination banks on said upper tier portions emitting light rays for a second predetermined interval, and selected ones of said illumination banks on said lower tier portions emitting light rays for a third predetermined interval.

9. The apparatus of claim 1 wherein each one of said first and second pluralities of light emitting means has a nominal wavelength and said acquisition means has a predetermined acquisition bandwidth, said nominal wavelength falling within said predetermined acquisition bandwidth to thereby improve acquisition means gain.

* * * * *